United States Patent
Tanaka et al.

(10) Patent No.: US 11,091,755 B2
(45) Date of Patent: Aug. 17, 2021

(54) METHOD OF BREEDING EUKARYOTE USING PROTEIN HAVING DOUBLE-STRANDED DNA CLEAVAGE ACTIVITY

(71) Applicant: KABUSHIKI KAISHA TOYOTA CHUO KENKYUSHO, Nagakute (JP)

(72) Inventors: Hidenori Tanaka, Nagakute (JP); Nobuhiko Muramoto, Nagakute (JP); Hiroki Sugimoto, Nagakute (JP); Tomoko Tanaka, Nagakute (JP)

(73) Assignee: KABUSHIKI KAISHA TOYOTA CHUO KENKYUSHO, Nagakute (JP)

( * ) Notice: Subject to any disclaimer, the term of this patent is extended or adjusted under 35 U.S.C. 154(b) by 0 days.

(21) Appl. No.: 15/854,339

(22) Filed: Dec. 26, 2017

(65) Prior Publication Data

US 2018/0179513 A1    Jun. 28, 2018

(30) Foreign Application Priority Data

Dec. 27, 2016  (JP) .............................. JP2016-254196

(51) Int. Cl.
| | |
|---|---|
| *C12N 15/01* | (2006.01) |
| *C12N 15/82* | (2006.01) |
| *C12N 9/22* | (2006.01) |
| *A01H 1/02* | (2006.01) |
| *A01H 1/06* | (2006.01) |

(52) U.S. Cl.
CPC .............. *C12N 15/01* (2013.01); *A01H 1/02* (2013.01); *A01H 1/06* (2013.01); *C12N 9/22* (2013.01); *C12N 15/8201* (2013.01); *C12N 15/8206* (2013.01); *C12N 15/8213* (2013.01)

(58) Field of Classification Search
None
See application file for complete search history.

(56) References Cited

U.S. PATENT DOCUMENTS

| | | |
|---|---|---|
| 2008/0166809 A1 | 7/2008 | Ohta et al. |
| 2011/0277189 A1 | 11/2011 | Kondo et al. |
| 2018/0163232 A1 | 6/2018 | Gao et al. |
| 2018/0184606 A1 | 7/2018 | Muramoto et al. |
| 2018/0371477 A1 | 12/2018 | Tanaka et al. |

FOREIGN PATENT DOCUMENTS

| | | |
|---|---|---|
| JP | 2006-141322 A | 6/2006 |
| JP | 2011-160798 A | 8/2011 |
| JP | 2012-044883 A | 3/2012 |
| JP | 2017-012145 A | 1/2017 |
| JP | 2017-099338 A | 6/2017 |
| JP | 2017-104082 A | 6/2017 |
| WO | 2016/155482 A1 | 10/2016 |

OTHER PUBLICATIONS

Ashraf et al (1993 Mutation Research 302:75-82 (Year: 1993).*
Lopes et al (2008 Brazilian Archives of Biology and Technology 51:27-34) (Year: 2008).*
Jinek et al. "A Programmable Dual-RNA-Guided DNA Endonuclease in Adaptive Bacterial Immunity". Science, vol. 337, Aug. 17, 2012, pp. 816-821 with supplemental materials.
Bio Catalog 2002-2003, Takara Shuzo Co., Ltd., 2003, "Fok I", pp. cover sheet and A-39.
Jan. 29, 2019 Office Action Issued in Japanese Patent Application No. 2016-254196.
Jun. 11, 2019 Office Action Issued in Japanese Patent Application No. 2016-254196.
"Fast Digest restriction enzyme." Cosmo Bio Co., Ltd., Jun. 1, 2019, 5 pages, url: https://www.cosmobio.co.jp/upfiles/catalog/pdf/catalog_11363.pdf.
Sep. 15, 2020 Office Action issued in Japanese Patent Application No. 2016-254196.

* cited by examiner

*Primary Examiner* — Brent T Page
(74) *Attorney, Agent, or Firm* — Oliff PLC

(57) ABSTRACT

A method includes introducing a protein having double-stranded DNA cleavage activity itself into the eukaryote or a part of the eukaryote, and rearranging DNA of the eukaryote by the protein in the eukaryote or a part of cells of the eukaryote.

20 Claims, 5 Drawing Sheets

Specification includes a Sequence Listing.

Break point sequence

Chr1 13257453   GTATTTTGT TTAA AGGAACCAC   Chr1 18450963
Chr3 01620101   CTATTAGTC TTAA TTCCGAAAA   Chr3 02161880
Chr4 16718658   CCAAATTTT TTAA TGGACATGT   Chr4 16950895
Chr1 28734201   AAAGTTTCG TTAA ACAAAATTG   Chr5 04690601

Break point sequence

Chr2 18950872   GTCTTAATC GCGC CATCGGAAC   Chr3 02153424
Chr5 20132781   GGGGAAGAA GCGC GATATGAGA   Chr3 02153424

1

METHOD OF BREEDING EUKARYOTE USING PROTEIN HAVING DOUBLE-STRANDED DNA CLEAVAGE ACTIVITY

TECHNICAL FIELD

The present teachings relate to a method of breeding a eukaryote using a protein having double-stranded DNA cleavage activity and the like.

DESCRIPTION OF RELATED ART

Conventional methods of breeding eukaryotes include methods of efficiently obtaining useful eukaryotes by simultaneously and/or successively cleaving genome DNA to induce genetic recombination and artificially rearrange the genome, to thereby create a population of diverse eukaryotes with diverse genomes.

For example, genetic transformation is induced by introducing DNA coding for a double-stranded DNA restriction enzyme such as a restriction enzyme from a thermophile into a eukaryote to thereby transform the eukaryote and cause the restriction enzyme to be expressed in cells, and then transiently raising a temperature or the like to transiently activate the enzyme and cleave genome DNA (Japanese Patent Applications Publication Nos. 2011-160798, 2006-141322, 2012-44883).

Because such genome rearrangement involves large-scale genetic recombination at one time, it is suited to improving quantitative traits such as plant productivity that involve multiple genes, and is advantageous for promoting rapid plant evolution.

CITATION LIST

[Patent Document 1] Japanese Patent Application Publication No. 2011-160798
[Patent Document 2] Japanese Patent Application Publication No. 2006-141322
[Patent Document 3] Japanese Patent Application Publication No 2012-44883.

SUMMARY

However, the inventors have found certain problems with existing methods. That is, even with these rearrangement techniques about 5 to 6 passages are required to obtain an individual expressing stable and consistent characteristics. Moreover, transient activation of the double-stranded DNA cleavage activity of the restriction enzyme is normally achieved through heat treatment at a temperature above an ordinary growth temperature of the eukaryote, considering an optimum temperature of the restriction enzyme. Such heat treatment puts a great deal of stress on plants, and may for example affect plant growth and yields in flowering plants, which are rather vulnerable to high temperatures during a reproductive growth phase.

Because these methods rely on transforming eukaryotes with genes coding for restriction enzymes, moreover, a certain amount of time is required for the restriction enzyme gene to be transcribed and translated so that the restriction enzyme can act as a restriction enzyme. On the other hand, if a restriction enzyme is expressed and acts continuously within a eukaryote, unanticipated genetic recombination may occur within the genome, and the growth and survival of the eukaryote may be adversely affected.

It is also necessary to remove the introduced gene from the cell or genome so that the restriction enzyme does not continue to be expressed in the transformant, and backcrossing and other forms of genetic separation are applicable to plants that propagate by seeds. However, many plants such as potatoes, strawberries, ornamental flowers, fruit trees and sugar cane that propagate vegetatively also have poor seed-forming ability, making genetic separation difficult. They are also highly heterogenous, so traits in seed-forming progeny may be different from those of the parent generation.

Thus, there have been various problems with genome rearrangement and breeding of eukaryotes by artificial simultaneous multiple genetic recombination through transformation with genes coding for restriction enzymes. The present teachings provide a more practical breeding technique.

Looking at conventional techniques of transformation with genes coding for restriction enzymes, the inventors focused on the possibility that various breeding problems may occur because this gene is incorporated into the eukaryote. After various researches, the inventors discovered that genome rearrangement could be promoted by cleaving genome DNA and inducing genetic recombination by supplying a restriction enzyme from the outside to a eukaryote rather than by causing the restriction enzyme to be expressed in the eukaryote. The present teachings provide the following means.

That is, the present teachings provide a method of breeding a eukaryote (hereunder sometimes called the breeding method of the teachings), comprising a step of introducing a protein having double-stranded DNA cleavage ability itself into the eukaryote or a part of the eukaryote, and a step of rearranging the DNA of the eukaryote by the protein within the eukaryote or a part of cells of the eukaryote.

Moreover, the present teachings also provide a method of producing a genetically modified eukaryote (hereunder sometimes called the production method of the teachings), comprising a step of an introducing a protein having double-stranded DNA cleavage ability itself into the eukaryote or a part of the eukaryote, and a step of rearranging DNA of the eukaryote by the protein within the eukaryote or a part of the cells of the eukaryote.

The present teachings also provide a method of rearranging the DNA of a eukaryote (hereunder sometimes called the rearrangement method of the teachings), comprising a step of introducing a protein having double-stranded DNA cleavage ability itself into the eukaryote or a part of the eukaryote, a step of rearranging DNA of the eukaryote by the protein within the eukaryote or a part of cells of the eukaryote.

Furthermore, the present teachings also provide a method of evaluating a eukaryote having DNA that has been rearranged by a restriction enzyme (hereunder sometimes called the evaluation method of the teachings), comprising a step of comparing a first DNA from the eukaryote before rearrangement with a second DNA from the rearranged eukaryote corresponding to the first DNA, and a step of detecting a recognition sequence of the restriction enzyme in the second DNA.

The means of the following embodiments including the means described above may be included in the present teachings.

[1] A method of breeding a eukaryote, comprising introducing a protein having double-stranded DNA cleavage ability itself into the eukaryote or a part of the eukaryote, and rearranging DNA of the eukaryote by the protein within the cells of the eukaryote or a part thereof.

[2] The method according to [1], wherein the protein is a restriction enzyme recognizing a 4-bp sequence.

[3] The method according to [2], wherein the restriction enzyme recognizes a base sequence selected from 16 kinds of 4-bp sequences having palindromic structures.

[4] The method according to any of [1] to [3], wherein the recognition sequence of the restriction enzyme is selected from the group consisting of TTAA, GATC, CCGG, ACGT, AATT, AGCT, GCGC, GGCC, GTAC and CGCG.

[5] The method according to any of [1] to [4], wherein the protein is a restriction enzyme selected from the group consisting of BstUI, AfaI, HaeIII, HinP1I, AluI, MluCI, HpyCH4IV, MspI, MboI and MseI.

[6] The method according to any of [1] to [5], wherein an optimum temperature for the double-stranded DNA cleavage activity of the protein is 25° C. or more and 40° C. or less.

[7] The method according to any of [1] to [6], wherein the restriction enzyme has double-stranded DNA cleavage ability that cleaves double-stranded DNA so as to produce sticky ends.

[8] The method according to any of [1] to [7], wherein the introducing employs an artificial method of protein introduction via the eukaryote or a part of the cell membrane of the eukaryote.

[9] The method according to any of [1] to [8], wherein the eukaryote is a plant.

[10] The method according to [9], wherein the introducing comprises bringing the protein into contact with a protoplast obtained from the plant in the presence of at least one kind of protein introduction agent.

[11] A method of producing a genetically modified eukaryote, the method comprising introducing a protein having double-stranded DNA cleavage ability itself into the eukaryote or a part of the eukaryote, and a rearranging the DNA of the eukaryote is rearranged by the protein within the cells of the eukaryote or a part thereof.

[12] A method of rearranging DNA of a eukaryote, the method comprising introducing a protein having double-stranded DNA cleavage ability itself into the eukaryote or a part of the eukaryote, wherein the DNA of the eukaryote is rearranged by the protein within the eukaryote or a part of the cells of the eukaryote.

[13] A method of evaluating a eukaryote having DNA that has been rearranged by a restriction enzyme, the method comprising comparing a first DNA from the eukaryote before rearrangement with a second DNA from the eukaryote after rearrangement corresponding to the first DNA, and detecting a recognition sequence of the restriction enzyme in the second DNA.

DETAILED DESCRIPTION OF INVENTION

The present teachings relate to a breeding technique involving rearrangement of eukaryotic DNA, and specifically relates to a breeding technique in which a protein having double-stranded DNA cleavage activity is itself introduced into a eukaryote or a part of the eukaryote to thereby rearrange the DNA of the eukaryote, and to a use therefor. It was discovered that according to this breeding method, the various problems of conventional methods can be resolved all at once by introducing a protein such as a restriction enzyme having double-stranded DNA cleavage activity itself into the eukaryote.

At least some of the following advantages can be obtained according to the technique of the teachings: (i) the steps taken to create an individual with a rearranged genome can be greatly reduced, (ii) activation treatment to activate the double-stranded DNA cleavage activity of the protein can be avoided, (iii) heat load associated with such activation treatment can be avoided, (iv) gene introduction and recombinant preparation can be avoided, (v) the technique is useful for creating diversity in highly heterogenous plants such as vegetatively propagating plants, and (vi) the technique can be applied to a wide range of eukaryotes because it does not involve gene introduction.

According to the technique of the teachings, a eukaryote population with a highly diverse genome composition and traits can be constructed easily and efficiently without going through transformation. This eukaryote population is thought to be a population of eukaryotes having traits acquired, improved, lost, reduced, modified or the like in various ways, such as eukaryotes that have acquired new traits that may occur in the course of evolution, those having traits lost or degraded, and improved.

Figure 1:
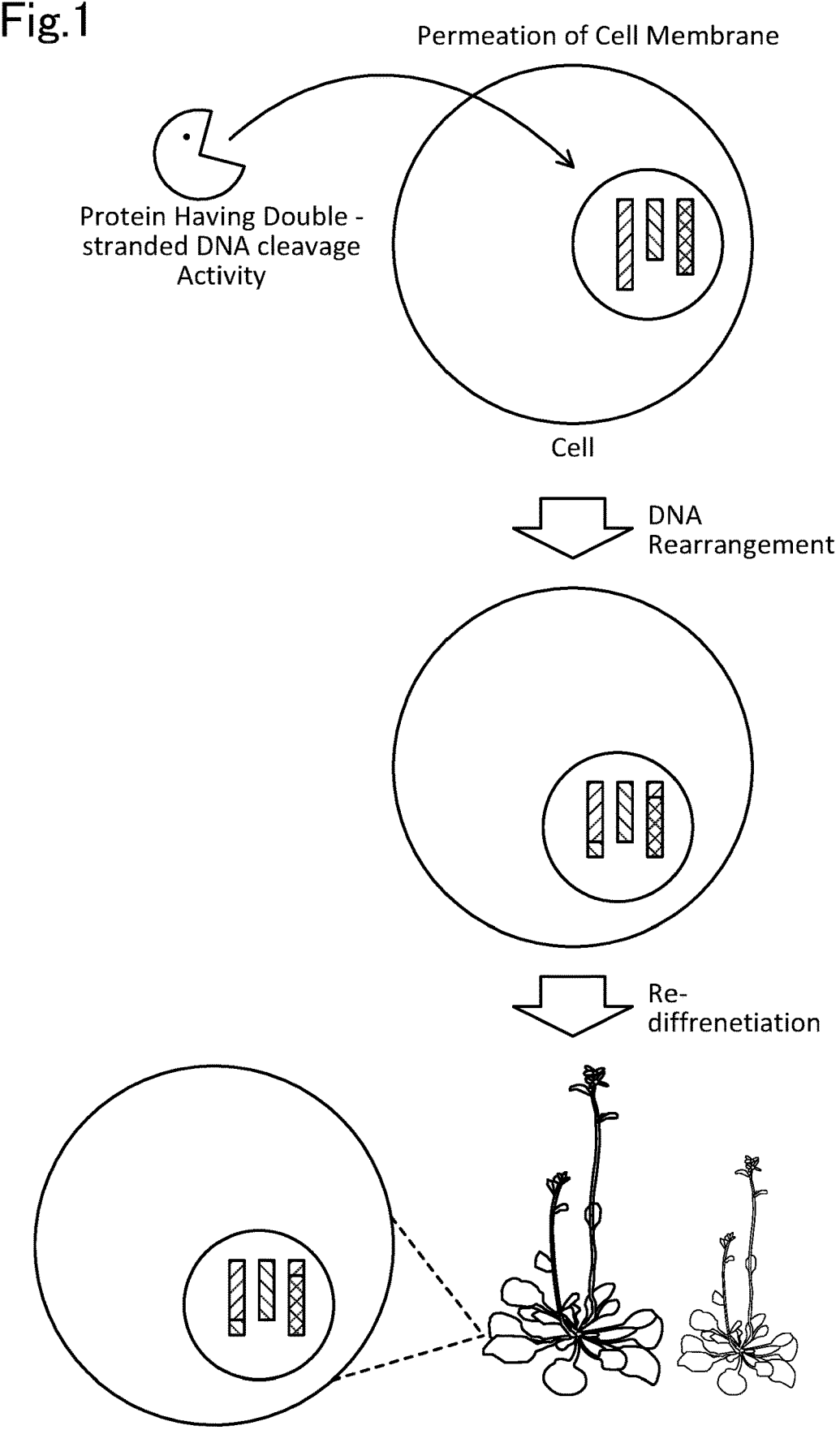
FIG. 1 shows an outline of a breeding method disclosed in the present teachings.
Figure 2:
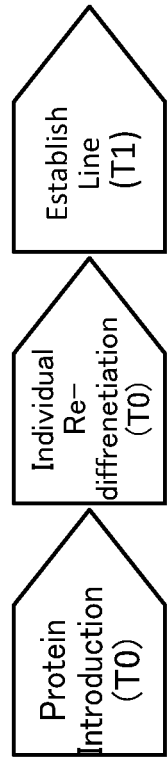
FIG. 2 shows a difference between numbers of steps required to obtain an individual with a rearranged genome in the breeding method disclosed in the present teachings and a conventional method.
Figure 2:
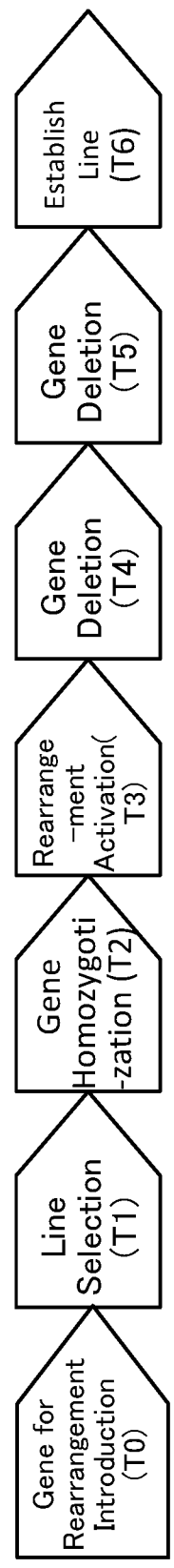

FIG. 1 shows an outline of the technique of the teachings, while FIG. 2 shows a comparison of the technique with a conventional method. The cells used in transformation are called a T0 generation, while an established line with fixed trait changes is called a T1 generation, and subsequent generations that have formed seeds are called T2, T3, T4, T5 and T6 generations. As shown in FIGS. 1 and 2, the technique of the teachings introduces a protein having double-stranded DNA cleavage activity into a plant cell such as a protoplast (protein introduction step (T0) in FIG. 2). The introduced protein can cleave genome DNA in the cells without the need for special activation, inducing genetic recombination and promoting rearrangement of genome DNA based on its inherent activity. It is thus possible to form protoplasts (a population) having various new genome compositions that are different from one another. After a certain period of time, the introduced protein is broken down by the proteolysis system in the cells, and does not function in the cells. Because the protein is deactivated by proteolysis or the like, the new genome composition is unique to that cell (protoplast).

These various protoplasts can then be re-differentiated by ordinary methods into plants to obtain a population of plants having diverse genome compositions at a fixed rate (individual re-differentiation step (T0) in FIG. 2).

Plants can then be selected based on predetermined indicators from plants having various traits and new genome compositions (line establishment step in FIG. 2). Because the selected plants have no exogenous genes coding for restriction enzymes, there is no need for gene separation, and consequently according to this breeding method a plant with fixed characteristics can be obtained simply by selecting a plant based on the desired characteristics from the resulting population.

By contrast, a lower part of FIG. 2 shows introduction of a gene coding for a restriction enzyme or the like. As shown in FIG. 2, for example a gene is introduced into a plant body such as a seed (rearrangement gene introduction step), individual plants are regenerated from this seed, and an individual plant having the introduced rearrangement gene is selected (line selection step (T1)). Next, selected plants are crossed with each other to obtain a plant that is homozygous for the rearrangement gene (gene homozygotization step (T2)). A plant (T3) obtained from the T2 seed is heat treated to activate the restriction enzyme and promote rearrangement of its genome composition (rearrangement activation step (T3)). The rearrangement gene is then removed in the subsequent T4 plant and T5 plant (rearrangement gene removal step (T4) and rearrangement gene removal step (T5)). A plant line having a useful trait can then be established (line establishment (T6)).

In the present teachings, "genome set" means DNA that is present as chromosomal DNA in a eukaryotic cell, is self-replicable in eukaryotic cells, and is transmitted to daughter cells.

In the present teachings, "genetic recombination" is used in a broad sense to mean phenomena of DNA cleavage and reassortment occurring between DNAs. Consequently, "genetic recombination" herein encompasses homologous recombination and heterologous recombination. Moreover, "genetic recombination" herein also encompasses genetic mutations involving substitution, insertion, deletion and the like of one or two or more bases, and chromosomal mutations such as chromosome inversion, unequal crossover, crossover, translocation, duplication, deletion, copy number decrease, copy number increase, chromosome polyploidization and chromosome aneuploidization. Moreover, "genetic recombination" herein encompasses both genetic recombination within the same chromosome and genetic recombination between different chromosomes.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and inventions to provide a further improved method of breeding a eukaryote using a protein having double-stranded DNA cleavage activity and the like.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the invention, separately from the constitution of features described in the Examples and/or Claims. Moreover, all descriptions of numerical ranges and groups or sets are intended to include intermediate configurations for purposes of restricting the initial disclosures and the claimed matter specifying the invention.

(Method for Breeding Eukaryote)

The breeding method of the teachings comprises introducing a protein having double-stranded DNA cleavage ability itself into the eukaryote or a part of the eukaryote, and rearranging DNA of the eukaryote by the protein within the eukaryote or a part of cells of the eukaryote.

(Eukaryote)

The breeding method of the teachings is applicable to any eukaryote. When the eukaryote is a multicellular organism, the introducing may be applied to a part of the eukaryote (such as a cell, tissue or organ as described below).

Examples of the eukaryotes applied to the breeding method of the teachings include animals, plants and eukaryotic microorganisms. The animals are not particularly limited, and examples include non-human mammals and various non-mammals such as fish. The animal to which the breeding method is applied may also be anything derived from an animal, and may be in the form of various kinds of cells, tissues, organs, unfertilized eggs, sperm, fertilized eggs and the like. For purposes of obtaining a modified animal, it is convenient if it is in a form such as a fertilized egg having an ability to regenerate into a complete animal.

The plants to which the breeding method is applied are also not particularly limited, and examples include dicotyledonous plants and monocotyledonous plants, such as those belonging to the Brassicaceae, Gramineae, Solanaceae, Leguminosae and Salicaceae (see below).

Brassicaceae: *Arabidopsis thaliana, Brassica rapa, Brassica napus, Brassica oleracea* var. *capitata, Brassica rapa* var. *pekinensis, Brassica rapa* var. *chinensis, Brassica rapa* var. *rapa, Brassica rapa* var. *hakabura, Brassica rapa* var. *lancinifolia, Brassica rapa* var. *peruviridis, Brassica rapa* var. *chinensis, Brassica Raphanus sativus, Wasabia japonica*, etc.

Solanaceae: Nicotiana tabacum, Solanum melongena, Solaneum tuberosum, Lycopersicon lycopersicum, Capsicum annuum, Petunia, etc.

Leguminosae: *Glycine max, Pisum sativum, Vicia faba, Wisteria floribunda, Arachis hypogaea, Lotus corniculatus* var. *japonicus, Phaseolus vulgaris, Vigna angularis, Acacia*, etc.

Asteraceae: *Chrysanthemum morifolium, Helianthus annuus*, etc.

Palmaceae: *Elaeis guineensis, Elaeis oleifera, Cocos nucifera, Phoenix dactylifera, Copernicia*, etc.

Anacardiaceae: *Rhus succedanea, Anacardium occidentale, Toxicodendron vernicifluum, Mangifera indica, Pistacia vera*, etc.

Cucurbitaceae: *Cucurbita maxima, Cucurbita moschata, Cucurbita pepo, Cucumis sativus, Trichosanthes cucumeroides, Lagenaria siceraria* var. *gourda*, etc.

Rosaceae: Amygdalus communis, Rosa, Fragaria, Prunus, Malus pumila var. domestica, etc.

Caryophyllaceae: *Dianthus caryophyllus*, etc.

Salicaceae: *Populus trichocarpa, Populus nigra, Populus tremula*, etc.

Gramineae: *Zea mays, Oryza sativa, Hordeum vulgare, Triticum aestivum, Phyllostachys, Saccharum officinarum, Pennisetum purpureum, Erianthus ravennae, Miscanthus virgatum, Sorghum, Panicum*, etc.

Liliaceae: *Tulipa, Lilium*, etc.

Myrtaceae: *Eucalyptus camaldulensis, Eucalyptus grandis*, etc.

The plant applied to the breeding method of the teachings may be any that is derived from a plant, but a form having an ability to regenerate a complete plant is convenient for obtaining a plant with a rearranged genome. Consequently, the plants may take any plant forms such as protoplasts, cells, various tissues, organs, leaves, seedlings, axillary buds, side buds, adventitious buds, flower buds and other shoots, shoot tops, stems, branches, pistils or ovules and parts thereof, stamens or pollen and parts thereof, seeds or embryos and parts thereof, roots or parts of roots, and callus.

The plant applied to the breeding method of the teachings is not particularly limited, and a wide variety of seed-propagating plants and vegetatively propagating plants and the like may be used. Of these, gene separation can be facilitated and traits can be stabilized by applying vegetative propagation to the plants. Examples of vegetatively propagating plants include various plants having vegetatively propagating organs, including plants in the lily family such as onions, garlic and lilies having bulbs, potatoes, cyclamen and the like having tubers, taro, water chestnut, gladiolus and the like having corms, lotus, bamboo shoots and the like having rhizomes, strawberries, saxifrage and the like having runners, sweet potatoes and the like having tuberous roots, *Metaplexis japonica* and the like having creeping roots, *Kalanchoe* and the like having adventitious buds at the edges of the leaves, *Dioscorea japonica, Laportea bulbifera*, tiger lily and the like having propagules, and yams and the like having rhizophores. Moreover, the breeding method of the teachings is also suited to plants that are vegetatively propagated for breeding purposes, such as fruit trees and other woody plants that are propagated by cutting and grafting, and sugar cane, ornamental flowers, cacti and the like that are propagated by cutting and root division.

The cells of plants have cell walls. Considering cell membrane permeability of the protein, it is suitable to use protoplasts when using a plant as the eukaryote in the breeding method of the teachings.

The microorganism is not particularly limited, but considering material production and the like, examples include microbial cells such as yeasts and molds such as koji mold. The koji mold may be an *Aspergillus* species such as *Aspergillus aculeatus* or *Aspergillus oryzae*. Various known yeasts may be used, and examples include *Saccharomyces* yeasts such as *Saccharomyces cerevisiae, Schizosaccharomyces* yeasts such as *Schizosaccharomyces pombe, Candida* yeasts such as *Candida shehatae, Pichia* yeasts such as *Pichia stipitis, Hansenula* yeasts, *Klocckera* yeasts, *Schwanniomyces* yeasts and *Yarrowia* yeasts, *Trichosporon* yeasts, *Brettanomyces* yeasts, *Pachysolen* yeasts, *Yamadazyma* yeasts, *Kluyveromyces* yeasts such as *Kluyveromyces marxianus* and *Kluyveromyces lactis*, and *Issatchenkia* yeasts such as *Issatchenkia orientalis*. Of these, a *Saccharomyces* yeast is preferred from the standpoint of industrial utility and the like, and *Saccharomyces cerevisiae* is especially desirable.

The yeast may be a heterothallic yeast or a homothallic yeast. In a case of the homothallic yeast, positive (superior) genetic recombination effects can be reinforced and negative genetic recombination effects can be excluded by means of spore breeding when a selecting is performed after the rearranging. Moreover, because it is possible to efficiently exclude yeasts carrying genome sets with negative genetic recombinations and obtain a population of homothallic yeasts carrying genome sets with positive genetic recombination effects, excellent genome rearrangement efficiency is possible even though the rearranging may be repeated once or more times.

(Introducing)

The introducing includes introducing a protein having double-stranded DNA cleavage ability itself into a eukaryote or a part thereof. The introducing in the breeding method of the teachings directly introduces the protein itself into a eukaryote or a part thereof."

(Protein Having Double-Stranded DNA Cleavage Activity: Protein of Teachings)

The protein of the teachings is not particularly limited, and a known double-stranded DNA cleavage enzyme may be used for example. Various features characterizing such proteins, such as an optimum temperature for double-stranded DNA cleavage activity, a recognition sequence and cleavage site, are not particularly specified when using the protein of the teachings as long as the protein is one capable of acting effectively on genome DNA or the like to cleave the DNA, inducing genetic recombination and rearranging the genome when supplied directly to a eukaryote or a part thereof.

(Recognition Sequence of Protein of Teachings)

There are no particular limitations on the recognition sequence when double-stranded DNA is cleaved by the double-stranded DNA cleavage enzyme. From the standpoint of recombination efficiency in the breeding method of the teachings, a roughly 4-bp or 5-bp sequence on the DNA is preferred as the recognition sequence. Such a protein of the teachings is so-called a frequent restriction enzyme. A number of cleavage sites on the genome also contributes to genome rearrangement efficiency. A protein having double-stranded DNA cleavage activity that recognizes a 6-bp sequence cannot adequately induce genetic recombination when introduced into a eukaryote. The protein of the teachings preferably recognizes a 4-bp sequence.

The protein of the teachings preferably recognizes a base sequence selected from 16 kinds of 4-bp sequences having palindromic structures. A recognition sequence with a palindromic structure tends to permit stable cleavage of double-stranded DNA. The palindromic structures here are a total of 16 kinds of sequences: AATT, ACGT, AGCT, ATAT, CATG, CCGG, CGCG, CTAG, GATC, GCGC, GGCC, GTAC, TATA, TCGA, TGCA and TTAA. A protein of the teachings such as a restriction enzyme having such a palindromic recognition sequence may be selected by a person skilled in the art from a commercially available restriction enzyme catalog.

For example, the protein of the teachings preferably recognizes any 4-bp sequence selected from the group consisting of TTAA, GATC, CCGG, ACGT, AATT, AGCT, GCGC, GGCC, GTAC and CGCG. All of these palindromic sequences can induce at least twice as much genetic recombination (BRCA1 expression) as controls (which do not induce genetic recombination). Examples of enzymes having these 10 palindromic sequences as recognition sequences are given in Table 1 below, but other restriction enzymes may also be used in the same way.

For example, a protein of the teachings that recognizes any 4-bp sequence selected from TTAA, GATC, CCGG, ACGT, AATT, AGCT and GCGC can induce at least 3 times as much genetic recombination as the controls. Moreover, for example, a protein of the teachings that recognizes any 4-bp sequence selected from TTAA, GATC, CCGG and ACGT can induce at least 4 times, or preferably at least 5 times, or more preferably at least 6 times, or still more preferably at least 7 times as much genetic recombination as the controls.

The cleavage site in the recognition sequence of the protein of the teachings is also not particularly limited, but is preferably one that cleaves so as to produce sticky ends for example. The reason for this is not entirely clear, but the inventors have found that restriction enzymes with cleavage modes that produce sticky ends rather than blunt ends tend to promote genetic recombination. For example, a sticky end may be a 2-bp end, a 4-bp end or a 2-bp sticky end. A protein of the teachings such as a restriction enzyme having such a cleavage site as a recognition sequence may be selected by a person skilled in the art from a commercially available restriction enzyme catalog.

For example, restriction enzymes that recognize the 4-bp palindromic sequences above and their cleavage ends are given below. These restriction enzymes are all suited to the breeding method of the teachings from the standpoint of the recognition sequence and the optimum temperature.

TABLE 1

Recognition Sequence of Restriction Enzyme and Form of Cleaved End

| Restriction Enzyme | Recognition Sequence | Cleaved End Form |
|---|---|---|
| AfaI | GT^AC | Blunt End |
| AluI | AG^CT | Blunt End |
| BstUI | CG^CG | Blunt End |
| HaeIII | GG^CC | Blunt End |
| MspI | C^CGG | 2 bp Sticky End |
| HpyCH4IV | A^CGT | 2 bp Sticky End |
| MseI | T^TAA | 2 bp Sticky End |
| HinP1I | G^CGC | 2 bp Sticky End |
| MboI | ^GATC | 4 bp Sticky End |
| MluCI | ^AATT | 4 bp Sticky End |

The optimum temperature for the double-stranded DNA cleavage activity of the protein of the teachings is not particularly limited, and may be any at which due to direct introduction of the protein DNA is cleaved and genetic recombination is induced within cells, but from the standpoint point of reducing or avoiding heat treatment, a restriction enzyme (hereunder called a cold restriction enzyme) having an optimum temperature (a temperature at which the protein has the greatest double-stranded DNA cleavage enzyme activity; also called an incubation temperature) in a low temperature range rather than a high temperature range may be used as the protein of the teachings. The high temperature range here may be a temperature range of 50° C. or more, or preferably 45° C. or more. That is, a cold restriction enzyme herein may be an enzyme having an optimum temperature for double-stranded DNA cleavage activity of less than 50° C., or preferably a restriction enzyme having an optimum temperature of less than 45° C. According to the cold restriction enzyme, heat treatment to cause the protein of the teachings to act on DNA can be reduced or avoided when introducing the protein of the teachings into a eukaryote or a part thereof, and problems due to the heat treatment can thus be reduced or avoided. This is also because the heat treatment should be avoided when introducing the protein of the teachings directly.

The cold restriction enzyme more preferably has an optimum temperature for double-stranded DNA cleavage activity in the normal temperature range. "Normal temperature range" here means 15° C. or more and 42° C. or less, or preferably 15° C. or more and 40° C. or less, or more preferably 25° C. or more and 40° C. or less, or still more preferably 25° C. or more and 37° C. or less, or yet more preferably 30° C. or more and not more than 37° C. or less.

In general, the cold restriction enzyme may have an optimum temperature of roughly 25° C. or more and 40° C. or less (typically, 25° C. or 37° C.). Moreover, in general the cold restriction enzyme can be deactivated by 15 minutes to 20 minutes of incubation at 60° C. to 70° C. The temperature at which the enzyme activity is deactivated by 15 minutes to 20 minutes of incubation is called a deactivation temperature. Even a cold restriction enzyme may have a deactivation temperature of 80° C. or more in some cases.

In the breeding method of the teachings, a restriction enzyme other than a cold restriction enzyme may be used as the protein of the teachings as long as genome rearrangement can be accomplished by directly introducing the protein of the teachings. For example, a restriction enzyme derived from a bacterium other than a thermophile (non-thermophilic bacteria-derived restriction enzyme) may be used. A thermophile is a bacterium with an optimum growth temperature of 45° C. or more and a growth limit temperature of 55° C. or more. Thermophiles are generally Archaea. A non-thermophilic restriction enzyme may generally be a cold restriction enzyme. On the other hand, a thermophilic restriction enzyme may generally have a deactivation temperature at a temperature of 80° C. or more. The optimum temperature of a thermophilic restriction enzyme is roughly 37° C. or more and 80° C. or less.

Because a cold restriction enzyme or non-thermophilic restriction enzyme has some degree of double-stranded DNA cleavage activity at the temperature at which it is normally applied to the eukaryote (growth temperature or culture temperature), the intensity (level) of the enzyme action can be set with a high degree of freedom by adjusting the various action conditions.

A commercially available restriction enzyme with an optimum temperature of roughly 25° C. or more and 40° C. or less (typically 25° C. or 37° C.) may be used as the cold restriction enzyme. For example, a commercially available restriction enzyme with such an optimum temperature and a deactivation temperature of 60° C. or more and not 70° C. or less may be used.

A known non-thermophilic restriction enzyme may also be selected and used appropriately as the non-thermophilic restriction enzyme.

Examples of such restriction enzymes are not particularly limited, but those recognizing 4-bp sequences include MluC1, HpyCH4IV, TaiI (MaeII), AluI, CviKI-1, FatI, CviAII, NlaIII, MspI, HpaII, BstUI, BfaI, DpnII, MboI, Sau3AI, DpnI, HinP1I, HhaI, HaeIII, PhoI, Csp6I, CviQI, RsaI, AfaI, TaqI, HpyCH4V and MseI. Examples of those recognizing 4-bp sequences and forming sticky ends include MluC1, HpyCH4IV, TaiI, FatI, CviAII, NlaIII, MspI, HpaII, BfaI, DpnII, MboI, Sau3AI, HinP1I, HhaI, Csp6I, CviQI, TaqI and MseI. Of these, those with an optimum temperature of 37° C. include MluC1, HpyCH4IV, AluI, CviKI-1, NlaIII, MspI, HpaII, BfaI, DpnII, MboI, Sau3AI, DpnI, HinP1I, HhaI, HaeIII, RsaI, AfaI, HpyCH4V and MseI. Those with an optimum temperature of 25° C. include CviAII, Csp6I and CviQI.

An enzyme other than these, or in other words a thermophilic restriction enzyme or a restriction enzyme with an optimum temperature of 50° C. or more, may also be used as the restriction enzyme. Even if such a restriction enzyme is applied at a temperature near the normal temperature range, it is still possible to cleave DNA in cells efficiently while avoiding adverse effects on the eukaryote by appropriately setting the conditions to adjust the intensity of the enzyme action. A known restriction enzyme may be used appropriately as such a restriction enzyme.

The optimum temperatures for the activities of proteins having double-stranded DNA cleavage activity such as restriction enzymes are described in protocols obtained with the enzymes, and can also be based on results of an enzyme reaction evaluation performed at various temperatures in the presence of a specific concentration of a specific substrate in buffer that is considered suitable for the enzyme.

For example, methods for measuring the optimum temperatures of restriction enzymes are described in the document (Greene, P. J., Poonian, M. S., Nussbaum, A. L., Tobias, L., Garfin, D. E., Boyer, H. W., & Goodman, H. M. (1975), Restriction and modification of a self-complementary octanucleotide containing the Eco RI substrate. Journal of Molecular Biology 99(2), 237-261). Specifically, cleavage of SV40 DNA ($^{32}$P labeled) by a restriction enzyme is quantitatively analyzed. That is, 5 µl of a restriction enzyme solution (0.05 M potassium phosphate buffer (pH 7.0), 0.02 M NaCl, 0.02% NP40, 0.1 mM EDTA, 0.7 mM β-mercaptoethanol, 0.7 pM restriction enzyme) is added to a total of 50 µl of a reaction solution (0.1 M Tris HCl (pH 7.5), 5 mM $MgCl_2$, 0.05 M NaCl 1.6 pM SV40 DNA), and restriction enzyme treatment is performed for a suitable time of about several minutes at various temperatures (temperatures set at suitable temperature intervals between about 0° C. and 80° C.). 1% SDS is added to stop the reaction, and supercoil DNA (form I), open circle DNA (form II) and linear DNA (form III) are isolated by agarose electrophoresis. A radiation dose (cpm) of each form is measured, and a number of phosphodiester bonds (pmol) cleaved by restriction enzyme treatment is determined by the following formula. The number of phosphodiester bonds cleaved at each temperature can then be graphed, and a temperature near the peak value can be taken as the optimum temperature (for double-stranded DNA cleavage activity) of the enzyme.

Phosphodiester bonds (pmol)=[2×(dose of form III (cpm)+dose of form II (cpm))/(total dose of forms *I*, *II* and *III* (cpm))]×amount of DNA (pmol)

The deactivation temperature of a protein such as a restriction enzyme having double-stranded DNA cleavage activity can be determined for example by maintaining the enzyme at various temperatures for about 15 minutes to 20 minutes and measuring the activity before and after heat treatment. The temperature at which activity is no longer detected is the deactivation temperature.

(Direct Introduction of Protein of Teachings into Eukaryote or a Part Thereof)

To cause the protein of the teachings to act on a eukaryote or a part thereof, the protein of the teaching is introduced directly into the eukaryote or a part thereof. The method of introducing the protein of the teachings into the eukaryote or a part thereof is not particularly limited. Techniques for introducing proteins into cells are themselves well known to those skilled in the art, and a person skilled in the art can appropriately select these from various known methods and apply them according to the introduction efficiency and the eukaryote that is the target of introduction and the like.

Methods of artificial protein introduction via eukaryotic cell membranes are preferably used for introducing proteins into cells and the like. The following are examples of such methods: methods using polyethylene glycol, electroporation, microinjection, transport by exosome-like vesicles, methods using cationic lipids, methods using peptides having both cell membrane permeability and the ability to form composites with proteins, and lipotransfection.

Methods using polyethylene glycol are disclosed for example in Woo, J. W., Kim, J., Kwon, S. I., Corvalán, C., Cho, S. W., Kim, H., Kim S. G., Kim, S. T., Choe, S., & Kim, J. S. et al., "DNA-free genome editing in plants with preassembled CRISPR-Cas9 ribonucleoproteins", Nature Biotechnology, 2015; 33, 1162-1164.

Electroporation methods are disclosed for example in Bulletin 1365 "Introduction of Proteins into Cells by Electroporation" (BioRad), and can also be implemented using systems and equipment such as a Neon (trade name) Transfection System (Invitrogen) or a NEPA21 electroporator (Nepagene).

Microinjection is a widely-used method of injecting proteins and the like into cells using a glass capillary, and is well known to those skilled in the art.

Methods using transport by exosome-like vesicles may be implemented using a commercial system such as a Gesicle system (Takara).

Methods using cationic lipids may be implemented for example using a commercially available system such as a BioPORTER Protein Delivery Reagent (Genlantis Inc.). That is, when a positively-charged BioPORTER/protein complex is added to cells, it binds to the surfaces of the negatively charged cells. Either the BioPORTER reagent fuses directly with the cell membranes and causes the captured protein to be absorbed by the cells, or else the BioPORTER/protein complex is incorporated into the endosome by endocytosis, and releases the captured protein into the cytoplasm. Because this is a simple transportation mechanism that does not involve further fusion or covalent bonding, it is considered effective for transporting active proteins into a variety of cell types. This method is disclosed for example in Zuris, J. A., Thompson, D. B., Shu, Y., Guilinger, J. P., Bessen, J. L., Hu, J. H., Maeder, M. L., Joung, J. K., Chen, Z. Y., and Liu, D. R. (2015), Cationic lipid-mediated delivery of proteins enables efficient protein-based genome editing in vitro and in vivo, Nature biotechnology, 33(1), 73-80.

Methods using peptides having both cell membrane permeability and the ability to form composites with proteins may be implemented for example using the commercially available "Prote-in" Transfection Reagent (Hygieia Bioscience), Xfect Protein transfection reagent (Clontech) or Pierce Protein Transfection Reagent (Thermo Fisher Scientific Inc.).

Lipotransfection methods are methods using vesicles with phospholipid bilayer membranes, and commercially available examples include Pro-DeliverIN CRISPR (OZ Biosciences).

In addition to those listed above, other commercially available examples include the ProteoJuice™ Protein Transfection Reagent (Merck KGaA), PULSin™ Protein, antibody and peptide delivery reagent (Polyplus-transfection SA), TransPass™ P Protein Transfection Reagent (New England Biolabs, Inc.) and Chariot (Active Motif) U.S. Pat. No. 6,841,535.

In the breeding method of the teachings, it is suitable to use a protein introduction agent that promotes cell membrane permeation by various proteins, such as polyethylene glycol, a cationic lipid, exosome-like vesicle, liposome or cell membrane permeable protein.

For the operations, solvents and other reagents and other conditions such as temperature and treatment time when introducing the protein of the teachings into a eukaryote or a part thereof, the conditions described in the manufacturer's protocols or in the document may be applied as is or with appropriate modifications according to the method used. The recognition sequence, cleavage site and optimum temperature of the protein of the teachings as well as the amount of the protein of the teachings used may be set appropriately according to the desired level of genome rearrangement, the type of eukaryote or a part thereof and the like.

The temperature and other conditions when introducing the protein of the teachings are not particularly limited, but a temperature lower than the optimum temperature for the double-stranded DNA cleavage activity of the protein of the teachings is preferable to a temperature near the optimum temperature. For example, if the optimum temperature for double-stranded DNA cleavage activity is about 37° C., the temperature during delivery is preferably 30° C. or less, or more preferably 25° C. or less.

When the eukaryote or a part thereof has a cell wall, it is preferable to remove the cell wall by a known method and use the eukaryote as a protoplast.

(Rearranging)

The rearranging includes rearranging the DNA of a eukaryote by the protein of the teachings within the eukaryote or a part of cells of the eukaryote. The protein of the teachings can exert double-stranded DNA cleavage activity within the cells of the eukaryote, cleave genome DNA and induce genetic recombination, and thereby cause reorganization of genome DNA or in other words genome rearrangement The rearranging may be repeated once or more times in order to exhibit the double-stranded DNA cleavage activity of the protein of the teachings. Various selecting may also be performed after the rearranging. Moreover, such a rearranging and selecting may also be performed multiple times.

Embodiments for causing the protein of the teachings to act in eukaryotic cells will be explained next. To produce the double-stranded DNA cleavage activity of the protein of the teachings or in other words to cause the protein of the teachings to act in eukaryotic cells, it is enough to simply apply the protein of the teachings under the growth conditions of the eukaryote. According to the breeding method of the teachings, the protein of the teachings acts immediately without the need for special activation because the protein of the teachings itself is introduced directly into the eukaryote. That is, the protein is thought to function as is in cells without the need for another process such as induction of gene expression or protein production. Moreover, problems due to unanticipated actions of the protein of the teachings can be reliably avoided because a protein is introduced from the outside and then decomposed or inactivated over a specific period of time.

The protein of the teachings tends to be highly heat sensitive, but the inventors have found that the protein of the teachings can be made to act on DNA without any special heat treatment or the like by growing (culturing) for a specific period of time under the inherent growth conditions of the eukaryote. The adverse effects of heat treatment on eukaryotes can be avoided because there is no heat treatment. As discussed above, a cold restriction enzyme is advantageous for ensuring recombination efficiency while avoiding heat treatment. From the standpoint of recombination efficiency, moreover, a restriction enzyme that recognizes a 4-bp sequence is advantageous for introducing the protein of the teachings directly. To control recombination efficiency, a non-thermophilic restriction enzyme as discussed above or a known thermophilic restriction enzyme may be used as the protein of the teachings without heat treatment.

When using a cold restriction enzyme, heat treatment may also be applied as necessary according to the double-stranded DNA cleavage activity of the protein of the teachings, such as by heat treating the eukaryote within the range of the inherent growth conditions of the eukaryote, or above these conditions, or near the upper limit of these conditions.

As the action conditions in terms of temperature for the protein of the teachings in the rearranging, these growth conditions are set according to the kind of eukaryote to be bred. In general, a temperature range including the normal temperature ranges of the various embodiments described above, for example, may be adopted as the inherent or suitable growth condition of the eukaryote. For example, the lower limit is preferably 10° C. or more, or more preferably 15° C. or more, and may be 20° C. or more, for example, or 25° C. or more, for example. The upper limit is preferably 47° C. or less, or more preferably 45° C. or less, or still more preferably 42° C. or less. It may also be 40° C. or less for example, or 37° C. or less for example, or 35° C. or less for example, or 30° C. or less for example. The range is preferably 10° C. or more and 47° C. or less, or more preferably 10° C. or more and 45° C. or less, or still more preferably 15° C. or more and 45° C. or less, or yet more preferably 20° C. or more and 42° C. or less, or most preferably 25° C. or more and 42° C. or less. The temperature in the rearranging can be set after considering the eukaryote to be used and the type of the protein of the teachings, as well as the desired recombination efficiency and the like.

The action time of the protein of the teachings in the rearranging is determined partly by the action temperature and the optimum temperature for the double-stranded DNA cleavage activity of the protein of the teachings. It is not particularly limited, but may be set to about 30 minutes or more and 72 hours or less for example. It may also be 1 hour or more for example, or 2 hours or more for example, or 3 hours or more for example, or 6 hours or more for example, or 8 hours or more for example, or 12 hours or more for example, or 18 hours or more for example, or 20 hours or more for example. It may also be 60 hours or less for example, or 48 hours or less for example, or 36 hours or less for example, or 24 hours or less for example. The range of the action time may be set by appropriately by combining the minimum and maximum times described above, and may be 1 hour or more and 72 hours or less for example, or 2 hours or more and 60 hours or less for example, or 2 hours or more and 48 hours or less for example, or 2 hours or more and 24 hours or less for example.

When the eukaryote is a plant, this rearranging may be performed by culturing a protoplast for about 1 hour to 4 hours at 20° C. to 30° C.

For purposes of selecting the protein of the teachings and setting the various action conditions in this rearranging, the genetic recombination effected by the protein of the teachings can be evaluated ahead of time in evaluating based on the expressed amount of a gene such as BRCA1 associated with gene repair or the level of homologous recombination using a GUS reporter gene. It is thus possible to select a suitable protein of the teachings and suitable conditions for obtaining the desired recombination efficiency.

If a eukaryote or a part thereof having a novel genome composition can be obtained in this way, this cell or the like can then be used by conventionally known methods to differentiate and/or regenerate the eukaryote or the like according to the kind of eukaryote, and obtained the desired eukaryote or a part thereof. To obtain the eukaryote as an individual, a cell or the like having regeneration ability can be used as the eukaryote or a part thereof into which the protein of the teachings is introduced.

Consequently, the present teachings may provide a method of evaluating a eukaryote breeding system, comprising introducing the protein of the teachings into a eukaryote or a part thereof, rearranging the DNA of the eukaryote with the protein of the teachings within all or a part of the cells of the eukaryote, and evaluating the action of the protein of the teachings based on genetic recombination in the eukaryote.

The present teachings may also provide a method of determining a protein of the teachings and/or its action conditions for use in a eukaryote breeding system, comprising introducing the protein of the teachings into a eukaryote or a part thereof, rearranging the DNA of the eukaryote with the protein of the teachings within the cells of all or a part of the eukaryote, and evaluating the action of the protein of the teachings based on genetic recombination in the eukaryote, after which the protein of the teachings and/or its action conditions are determined for use in that system based on the evaluation.

With such rearranging, the genome DNA of the eukaryote is rearranged and the eukaryote acquires a new genome composition without any gene introduction. Because the protein of the teachings is removed from the eukaryote or a part thereof by the inherent decomposition system of the eukaryote, it is not necessary to remove the protein of the teachings, and because the new genome composition is fixed in the cells, it is possible to eliminate the numerous breeding that were performed by gene introduction in the past. Because the protein of the teachings is introduced directly into the eukaryote or a part thereof, moreover, it can be made to act on DNA without any special activation treatment such as heat treatment, so that the burden of activation treatment on the eukaryote is eliminated or controlled. This is advantageous for breeding vegetatively propagating plants because cells or the like having the new genome composition can be regenerated from a plant body.

The breeding method of the teachings can be implemented as a method of producing a genetically modified eukaryote, or in other words a eukaryote with a modified genome composition. This breeding method may also be implemented as a method of rearranging the DNA of a eukaryote.

(Method of Evaluated Eukaryote with DNA Rearranged by Restriction Enzyme)

The present teachings may also provide a method of evaluating a eukaryote whose DNA has been rearranged by a restriction enzyme, comprising comparing a first DNA from the eukaryote before rearrangement with a second DNA from the eukaryote after rearrangement corresponding to the first DNA, and detecting a recognition sequence of the restriction enzyme in the second DNA.

In the breeding method of the teachings, the protein of the teachings is introduced directly into cells, cleaves genome DNA without any special activation treatment for example, and induces genetic recombination to rearrange genome DNA. Consequently, DNA cleavage activity other than that of the protein of the teachings on genome DNA is suppressed in the eukaryote, and other DNA rearrangement is not induced. Consequently, the genetic recombination site in the breeding method of the teachings can be inferred in advance, and it is possible to clearly detect extent and frequency of genetic recombination at the recognition sequence of the protein of the teachings in genome DNA.

Consequently, by comparing the genome DNA or the like of the eukaryote before and after rearrangement at the same site, it is possible to verify the recognition sequence of the protein of the teachings in the rearranged DNA, and confirm where the DNA has been cleaved and where genetic recombination has occurred. With this evaluation method, it is possible to obtain new findings about chromosomes and genome DNA.

EXAMPLES

Some of specific examples of the disclosure of the present teachings will be explained below. The following examples are for explaining the disclosure, and do not limit its scope.

Example 1

(Isolation of Mesophyll Protoplasts from Plant Body)

Protoplasts were isolated from *Arabidopsis thaliana* by a partially modified version of a method of Kim et al. (*Arabidopsis* mesophyll protoplasts: a versatile cell system for transient gene expression analysis. Nature protocols, 2007; 2(7), 1565-1572, Yoo, S. D., Cho, Y. H., & Sheen, J.).

Leaves were excised from 4- to 5-week-old plants, finely chopped with a razor blade, and placed in an enzyme solution (20 mM MES (pH 5.7), 1.5% (w/v) cellulase R10, 0.4% (w/v) macerozyme R10, 0.4 M mannitol, 20 mM KCl, 10 mM $CaCl_2$, 0.1% BSA), and the enzyme solution was deaerated for 30 minutes to cause it to permeate the leaves. This was then allowed to stand for 3 hours under shade at room temperature to release the protoplasts from the leaves. W5 solution (2 mM MES (pH 5.7), 154 mM NaCl, 125 mM $CaCl_2$, 5 mM KCl) was added in the same amount as the enzyme solution to stop the enzyme digestion reaction, and the protoplast solution was filtered (50 mm mesh filter) and then the filtered protoplast solution was centrifuged for 2 minutes at 100×g to remove plant residues. The collected protoplasts were suspended in W5 solution, and the suspension was allowed to stand on ice to naturally precipitate the normal protoplasts, which were then collected and suspended in MMG solution (4 mM MES (pH 5.7), 0.4 M mannitol, 15 mM $MgCl_2$), and used in the following restriction enzyme introduction test. The number of cells used was between $1 \times 10^4$ and $1 \times 10^6$.

Example 2

(Introduction of Restriction Enzyme into Protoplasts, and Genetic Recombination by Restriction Enzyme)

Protoplasts were isolated from *Arabidopsis thaliana* by a partially modified version of the method of Kim et al. (*Arabidopsis* mesophyll protoplasts: a versatile cell system for transient gene expression analysis. Nature protocols, 2007; 2(7), 1565-1572, Yoo, S. D., Cho, Y. H., & Sheen, J.). 100 U of each of the restriction enzymes to be used in this test (Takara or New England Biolabs, Inc., shown below) was added to a tube, and mixed by tapping with 200 ml of the isolated protoplasts. 210 ml of transfection solution (40% (w/v) PEG 4000 in $ddH_2O$, 0.4 M mannitol, 100 mM $CaCl_2$) was added and mixed by inversion to make the contents homogenous. This was left standing for 10 minutes at room temperature, 1 ml of WI solution was added to stop transfection, and the transfected protoplasts were collected by 3 minutes of centrifugation at 100×g, suspended in WI solution (4 mM MES (pH 5.7), 0.5 M mannitol, 20 mM $CaCl_2$), and cultured for 2 hours to 3 hours at room temperature (22° C. to 25° C.). The restriction enzymes used are shown below.

Restriction enzymes with 6-bp recognition sequences: BamHI (30° C. to 37° C.), EcoRI (37° C.), PstI (37° C.), SmaI (25° C.), SnaBI (37° C.), SphI (37° C.), XbaI (37° C.), XhoI (37° C.)

Restriction enzymes with 4-bp recognition sequences: BstUI (60° C.), AfaI (37° C.), HaeIII (37° C.), HinP1I (37° C.), AluI (37° C.), MluCI (37° C.), HpyCH4IV (37° C.), MspI (37° C.), MboI (37° C.), MseI (37° C.)

TABLE 2

Recognition Sequence of Restriction Enzyme and Form of Cleaved End

| Restriction Enzyme | Recognition Sequence | Cleaved End Form |
| --- | --- | --- |
| AfaI | GT^AC | Blunt End |
| AluI | AG^CT | Blunt End |
| BstUI | CG^CG | Blunt End |
| HaeIII | GG^CC | Blunt End |
| MspI | C^CGG | 2 bp Sticky End |
| HpyCH4IV | A^CGT | 2 bp Sticky End |
| MseI | T^TAA | 2 bp Sticky End |
| HinP1I | G^CGC | 2 bp Sticky End |
| MboI | ^GATC | 4 bp Sticky End |
| MluCI | ^AATT | 4 bp Sticky End |

Example 3

(Confirming Double-Stranded DNA Cleavage Effects of Restriction Enzyme in Protoplasts)

Following transfection, protoplasts that have been cultured at room temperatures can be centrifuged for 3 minutes at 100×g, and stored by freezing in liquid nitrogen after removal of the supernatant. To confirm the double-stranded DNA cleavage (double strand break: DSB) effects of the restriction enzyme, RNA was then extracted from the transfected protoplasts, and analyzed for expression of the BRCA1 gene, which is an important factor in DNA break repair (Characterization of *Arabidopsis thaliana* ortholog of the human breast cancer susceptibility gene 1: AtBRCA1, strongly induced by gamma rays. Nucleic acids research, 2003; 31(4), 1148-1155. Lafarge, S., & Montané, M. H.). RNA extraction was performed using an RNeasy Plant Mini Kit (Qiagen) according to the manufacturer's protocols.

cDNA was synthesized with a reverse transcription kit from the extracted RNA, and real-time PCR analysis was performed with a Power SYBR Green PCR master mix (Life Technologies Corporation). The reverse transcription reaction and real time PCR analysis were performed according to the procedures indicated by the manufacturers. 18S rRNA (detection primer; SEQ ID NOS:1 and 2) was measured as an internal standard, and the expressed amount of the DSB repair gene BRCA1 (detection primer; SEQ ID NOS:3 and 4) was also analyzed. The expressed amount of BRCA1 is shown as a relative value (expressed amount of BRCA1 in sample/expressed amount of 18S rRNA in sample). The results are given in FIGS. 3 and 4.

18SrRNA-F:
(SEQ ID NO: 1)
CGGCTACCACATCCAAGGAA

18SrRNA-R:
(SEQ ID NO: 2)
TGTCACTACCTCCCCGTGTCA

-continued

BRCA1-F:
(SEQ ID NO: 3)
CCATGTATTTTGCAATGCGTG

BRCA1-R:
(SEQ ID NO: 4)
TGTGGAGCACCTCGAATCTCT

Figure 3:
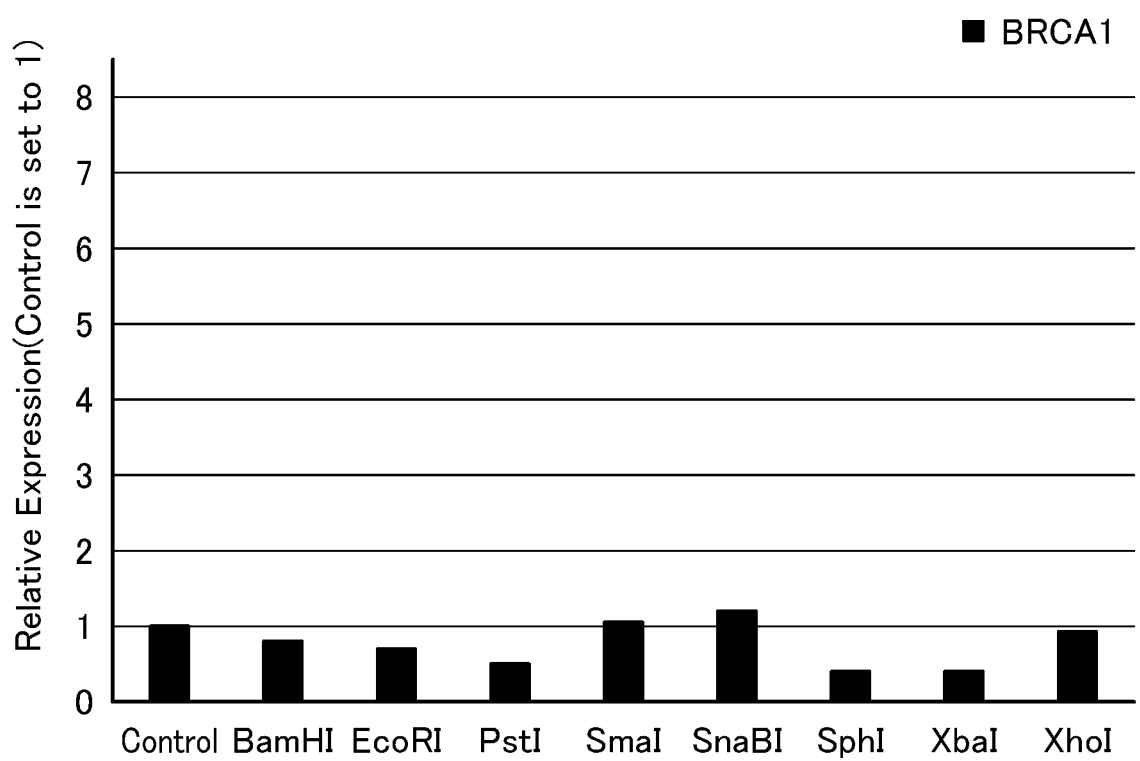
FIG. 3 shows expressed amounts of BRCA1 following introduction of cold frequent restriction enzymes recognizing 6-bp sequences.
Figure 4:
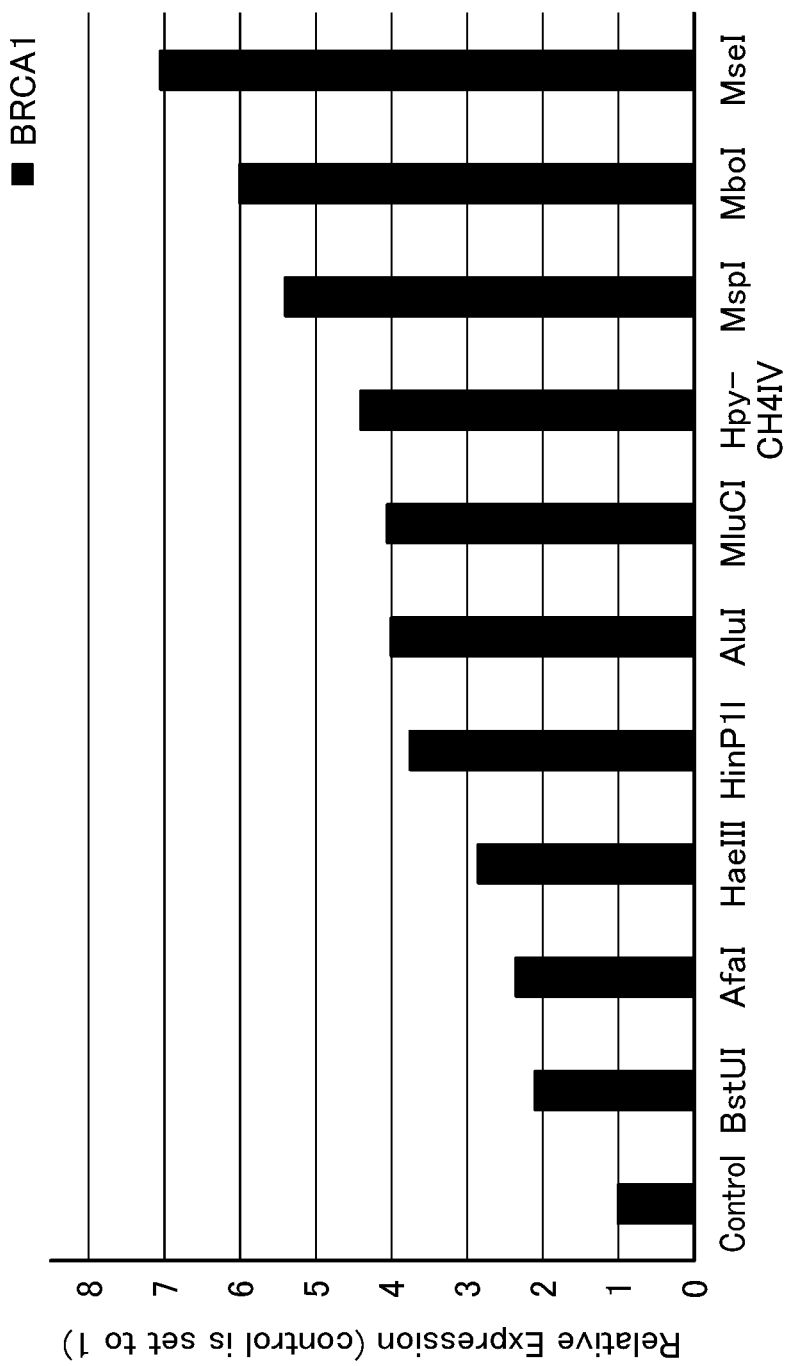
FIG. 4 shows expressed amounts of BRCA1 following introduction of cold frequent restriction enzymes recognizing 4-bp sequences.

As shown in FIG. 3, with the restriction enzymes having 6-bp recognition sequences (BamHI, EcoRI, PstI, SmaI, SnaBI, SphI, XbaI and XhoI) a remarkable increase in the expressed amount of BRCA1 (to at least twice the expression level of the untreated group) was not seen. As shown in FIG. 4, moreover, when the restriction enzymes having 4-bp recognition sequences (BstUI, AfaI, HaeIII, HinP1I, AluI, MluCI, HpyCH4IV, MspI, MboI and MseI) were introduced into protoplasts, a dramatic rise in BRCA1 expression to twice or more of the expression level of the untreated group (control) was seen with each enzyme. When the heat-resistant restriction enzyme TaqI was introduced, the expression level was roughly the same as in the control group (1.05× control group).

It can be seen from the results of FIG. 4 that the restriction enzymes that recognize 4-bp sequences and leave 2-base or 4-base sticky ends exhibit a greater increase in BRCA expression, so these cleavage structures appear to be advantageous. Moreover, with an enzyme that recognizes a 4-bp sequence it is possible to obtain twice or more of the BRCA expression as with the control, and restriction enzymes that recognize palindromic sequences such as TTAA, GATC, CCGG, ACGT, AATT, AGCT, GCGC, GGCC, GTAC and CGCG, such as typically BstUI, AfaI, HaeIII, HinP1I, AluI, MluCI, HpyCH4IV, MspI, MboI and MseI, are especially desirable. Moreover, some restriction enzymes that recognize TTAA, GATC, CCGG, ACGT, AATT, AGCT and GCGC exhibit 3 times or more of the BRCA expression of the control, and typical examples of these include HinP1I, AluI, MluCI, HpyCH4IV, MspI, MboI and MseI. Moreover, restriction enzymes that recognize the base sequences TTAA, GATC, CCGG and ACGT exhibit 4 times or more of the BRCA expression of the control, and typical examples are HpyCH4IV, MspI, MboI and MseI.

The recognition sequences and cleavage end types (blunt or sticky) of the enzymes used in these examples were quite various, and it appears that a restriction enzyme with a 4-bp recognition sequence and an optimum activity temperature of 25° C. to 37° C. can dramatically raise BRCA1 expression regardless of the type of enzyme (Table 1). These results suggest that when a 4-bp recognition type cold restriction enzyme protein is introduced into protoplasts it can cause double-stranded DNA cleavage without requiring heat treatment or other enzyme activations. Induction of genome rearrangement is associated with a rise in the expression of BRCA1 and other repair genes, suggesting that genome rearrangement is induced by introduction of the restriction enzyme into the protoplasts.

Figures 5, 6, 7:
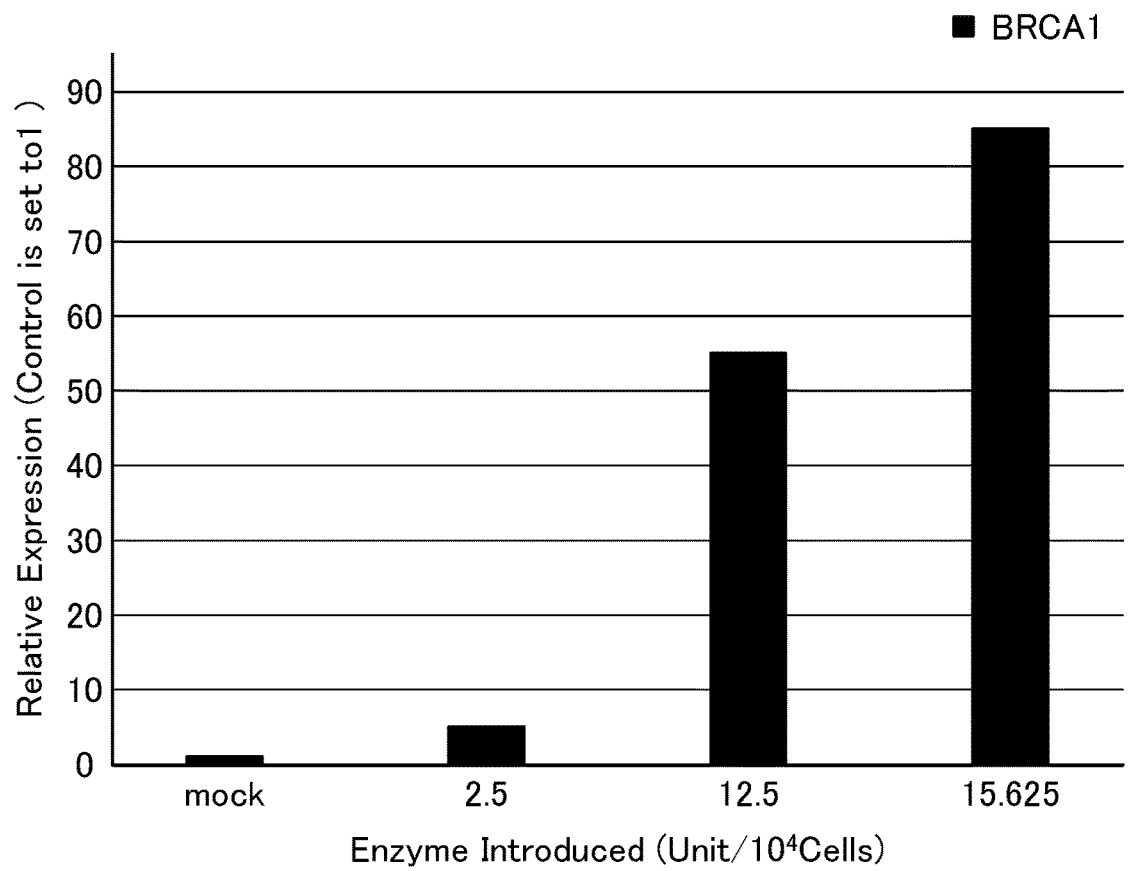
FIG. 5 shows the expressed amount of BRCA1 following introduction of a cold frequent restriction enzyme MseI.
FIG. 6 shows characteristics of a sequence subjected to genome rearrangement with the cold frequent restriction enzyme MseI.
FIG. 7 shows the characteristics of a sequence subjected to genome rearrangement with the cold frequent restriction enzyme Hinp1I.

The expressed amount of BRCA1 was also evaluated when increasing amounts of the restriction enzyme were added to the same amount of cells (MseI: 2.5, 12.5, 15.625 Unit/$10^4$ cells). The results are shown in FIG. 6. As shown in FIG. 6, the expressed amount of BRCA1 increased dramatically. These results show that a degree of the induced genome rearrangement can be controlled by adjusting the amount of the enzyme.

Example 4

(Re-Differentiation of Plant Body from Protoplast)

A plurality of steps is involved in re-differentiating a plant body from a protoplast. The protoplast is first proliferated and shoot differentiation is induced, after which root differentiation is induced to obtain a plant body. In plants that propagate by seed, the plant can then be transplanted to earth to obtain a next-generation seed (Characterization of the early events leading to totipotency in an *Arabidopsis* protoplast liquid culture by temporal transcript profiling. The Plant Cell; 2013; 25(7), 2444-2463. Chupeau, M. C., Granier, F., Pichon, O., Renou, J. P., Gaudin, V., & Chupeau, Y.). Specifically, a plant body may be obtained by the following methods for example (DNA-free genome editing in plants with preassembled CRISPR-Cas9 ribonucleoproteins. Nature Biotechnology, 2015; 33, 1162-1164. Woo, J. W., Kim, J., Kwon, S. I., Corvalán, C., Cho, S. W., Kim, H., Kim S. G., Kim, S. T., Choe, S., & Kim, J. S.).

Protoplasts with a restriction enzyme introduced therein are suspended in 0.5×B5 liquid medium (0.5×B5 mixed salts, 375 mg/l $CaCl_2 \cdot 2H_2O$, 18.35 mg/l NaFe-EDTA, 270 mg/l sodium succinate, 103 g/l sucrose, 0.2 mg/l 2,4-dichlorophenoxyacetic acid (2,4-D), 0.3 mg/l 6-benzylaminopurine (BAP) and 0.1 g/l MES), mixed with low-melting-point agarose to a final concentration of 1.2%, and spread on 6-well plates. 0.5×B5 liquid medium is laid over the solidified agarose medium, and allowed to stand in the dark for 7 days at 22° C. The liquid medium is changed appropriately as the protoplasts are cultured under light conditions (16 hours light/8 hours darkness) until microcallus of several millimeters in diameter is formed.

The microcallus is then transferred to MS re-differentiation medium (MS mixed salts, 30 g/l sucrose, 0.6% plant agar, 0.1 mg/l α-naphthalaneacetic acid (NAA), 0.5 mg/l BAP) and cultured until shoots form. Root differentiation is then induced in hormone-free 0.5×MS medium (0.5×MS mixed salts, 30 g/l sucrose), and the plants are transplanted to earth for seed formation, to obtain next-generation seeds.

Example 5

(Detection of Genome-Rearranged Individuals)

In the plant bodies obtained from re-differentiation, the sequences of large-scale genome re-arrangement sites were specified with high resolution at the nucleotide level by next-generation sequencer analysis. The sequences of the large-scale genome re-arrangement sites induced by the method of the teachings were shown to include restriction enzyme recognition sequences. As shown in FIG. 7, for example, when MseI with the recognition sequence TTAA was introduced, rearrangement occurred in a region straddling TTAA. Moreover, as shown in FIG. 7, for example, when HinP1I with the recognition sequence GCGC was introduced, rearrangement occurred in a region straddling GCGC. It was also shown that the pairs of rearranged chromosomes could be the same chromosomes or different chromosomes.

[Sequence Table Free Text]
SEQ ID NOS:1 to 4: Primers

The invention claimed is:

1. A method, the method comprising:
   introducing a protein having double-stranded DNA cleavage ability into cells of a plant, the protein being at least one restriction enzyme recognizing a 4-bp sequence selected from the group consisting of 5'-GATC-3', 5'-CCGG-3', 5'-ACGT-3', 5'-AATT-3', 5'-AGCT-3', 5'-GCGC-3', 5'-GTAC-3' and 5'-CGCG-3' and having double-stranded DNA cleavage ability that cleaves double-stranded DNA, wherein the introducing comprises bringing the protein into contact with a cell obtained from the plant in the presence of at least one kind of protein introduction agent;
   cleaving genome DNA simultaneously and successively by the protein and inducing repairing genome DNA within the cell, and thereby rearranging genome DNA of the plant cells by one or more genomic recombinations selected from the group consisting of chromosome inversion, unequal crossover, crossover, translocation, duplication, deletion, copy number decrease, copy number increase, chromosome polyploidization, chromosome aneuploidization, and genetic recombination between different chromosomes;
   re-differentiating the cell into plants to obtain a population of plants having diverse genome compositions; and
   selecting and breeding a plant having a desired characteristic from the population of the plants obtained by re-differentiating; wherein
      an optimum temperature for the restriction enzyme's double-stranded DNA cleavage activity of the protein is 25° C. or more and 40° C. or less.

2. The method according to claim 1, wherein the recognition sequence of the restriction enzyme is selected from the group consisting of 5'-GATC-3', 5'-CCGG-3', 5'-ACGT-3', 5'-AATT-3', 5'-AGCT-3' and 5'-GCGC-3'.

3. The method according to claim 2, wherein the restriction enzyme is selected from the group consisting of HinP1I, AluI, MluCI, HpyCH4IV, MspI, and MboI.

4. The method according to claim 1, wherein the introducing further comprises employing an artificial method of protein introduction via the cell membranes of the plant.

5. The method according to claim 1, wherein the at least one kind of protein introduction agent is selected from the group consisting of polyethylene glycol, a cationic lipid, an exosome-like vesicle, a liposome and a cell membrane permeable protein.

6. The method according to claim 1, wherein the recognition sequence of the restriction enzyme is selected from the group consisting of 5'-GATC-3', 5'-CCGG-3' and 5'-ACGT-3'.

7. The method according to claim 1, wherein the restriction enzyme is selected from the group consisting of HpyCH4IV, MspI, and MboI.

8. The method according to claim 1, wherein the introducing employs an artificial method of protein introduction excluding electroporation.

9. The method according to claim 1, wherein the rearranging rearranges the genome DNA by a plurality of the genomic recombination between a plurality of different chromosomes.

10. The method according to claim 1, wherein the cleaving induces increasing BRCA gene expression to three or more of the expression level of untreated cell.

11. A method, the method comprising:
   introducing a protein having double-stranded DNA cleavage ability into cells of a plant, the protein being at least one restriction enzyme recognizing a 4-bp sequence selected from the group consisting of 5'-GATC-3', 5'-CCGG-3', 5'-ACGT-3', 5'-AATT-3', 5'-AGCT-3' and 5'-GCGC-3' and having double-stranded DNA cleavage ability that cleaves double-stranded DNA, wherein the introducing comprises bringing the protein into contact with a cell obtained from the plant in the presence of at least one kind of protein introduction agent;
   cleaving genome DNA simultaneously and successively by the protein and inducing repairing genome DNA within the cell so as to increase BRCA gene expression to three or more of the expression level of untreated cell, and thereby rearranging genome DNA of the plant cells by one or more genomic recombination selected from the group consisting of chromosome inversion, unequal crossover, crossover, translocation, duplication, deletion, copy number decrease, copy number increase, chromosome polyploidization, chromosome aneuploidization, and genetic recombination between different chromosomes;
   re-differentiating the cell into plants to obtain a population of plants having diverse genome compositions; and
   selecting a plant having a desired characteristic from the population of the plants obtained by re-differentiating; wherein
      the restriction enzyme is selected from the group consisting of HinP1I, AluI, MluCI, HpyCH4IV, MspI, and MboI.

12. The method according to claim 11, wherein the restriction enzyme is selected from the group consisting of HinP1I, AluI, MluCI, HpyCH4IV, MspI, and MboI.

13. The method according to claim 11, wherein the restriction enzyme is selected from the group consisting of AluI, MluCI, HpyCH4IV, MspI, and MboI.

14. The method according to claim 12, wherein the restriction enzyme is selected from the group consisting of HpyCH4IV, MspI, and MboI.

15. The method according to claim 11, wherein the restriction enzyme is provided to 1 to 20 Unit per $10^4$ cells of the plant.

16. A method, the method comprising:
   introducing a protein having double-stranded DNA cleavage ability into cells of a plant, the protein being at least one restriction enzyme selected from the group consisting of HinP1I, AluI, MluCI, HpyCH4IV, MspI, and MboI, wherein the introducing comprises bringing the protein into contact with a cell obtained from the plant in the presence of at least one kind of protein introduction agent;

cleaving genome DNA simultaneously and successively by the protein and inducing repairing genome DNA and thereby rearranging genome DNA of the plant cells by one or more genomic recombination selected from the group consisting of chromosome inversion, unequal crossover, crossover, translocation, duplication, deletion, copy number decrease, copy number increase, chromosome polyploidization, chromosome aneuploidization, and genetic recombination between different chromosomes;

re-differentiating the cell into plants to obtain a population of plants having diverse genome compositions; and selecting and breeding a plant having a desired characteristic from the population of the plants obtained by re-differentiating, wherein the restriction enzyme is provided to 1 to 20 Unit per $10^4$ cells of the plant.

17. The method according to claim 16, wherein the inducing increases BRCA gene expression to four or more of the expression level of untreated cell.

18. The method according to claim 17, wherein the restriction enzyme is selected from the group consisting of HpyCH4IV, MspI, and MboI.

19. The method according to claim 17, wherein the restriction enzyme is selected from the group consisting of AluI, MluCI, HpyCH4IV, MspI, and MboI.

20. The method according to claim 1, wherein the restriction enzyme is selected from the group consisting of BstUI, AfaII, HinP1I, AluI, MluCI, HpyCH4IV, MspI, and MboI.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cggctaccac atccaaggaa                                            20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
tgtcactacc tccccgtgtc a                                          21

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ccatgtattt tgcaatgcgt g                                          21

<210> SEQ ID NO 4
<211> LENGTH: 21
```

```
<212> TYPE: DNA
<213> ORGANISM: Artificial Sequence
<220> FEATURE:
<223> OTHER INFORMATION: Primer

<400> SEQUENCE: 4
tgtggagcac ctcgaatctc t                                        21
```